(12) United States Patent
Liew

(10) Patent No.: US 12,296,331 B2
(45) Date of Patent: May 13, 2025

(54) FLUID COLLECTION DEVICE

(71) Applicant: WOHLTEC MEDICAL SDN BHD, Ipoh Perak (MY)

(72) Inventor: Yew Aw Liew, Ipoh Perak (MY)

(*) Notice: Subject to any disclaimer, the term of this patent is extended or adjusted under 35 U.S.C. 154(b) by 1043 days.

(21) Appl. No.: 17/283,560

(22) PCT Filed: Aug. 30, 2019

(86) PCT No.: PCT/MY2019/050051
§ 371 (c)(1),
(2) Date: Apr. 8, 2021

(87) PCT Pub. No.: WO2020/085893
PCT Pub. Date: Apr. 30, 2020

(65) Prior Publication Data
US 2021/0387178 A1    Dec. 16, 2021

(30) Foreign Application Priority Data

Oct. 23, 2018    (MY) .................... PI 2018703918

(51) Int. Cl.
*A61B 10/00*    (2006.01)
*B01L 3/00*    (2006.01)

(52) U.S. Cl.
CPC ........ *B01L 3/5021* (2013.01); *A61B 10/0051* (2013.01); *A61B 10/007* (2013.01); *A61B 2010/008* (2013.01); *B01L 2400/0478* (2013.01)

(58) Field of Classification Search
CPC .. B01L 3/5021; B01L 2400/0478; B01L 3/56; B01L 3/502; B01L 2200/141; A61B 10/0051; A61B 10/007; A61B 2010/008; A61B 5/15; A61B 10/0045

USPC ........................................................ 600/576
See application file for complete search history.

(56) References Cited

U.S. PATENT DOCUMENTS

| | | | |
|---|---|---|---|
| 701,671 A * | 6/1902 | Billings ............. | A61M 5/31511 604/218 |
| 3,706,305 A | 12/1972 | Berger et al. | |
| 2003/0105414 A1 | 6/2003 | Leong | |
| 2004/0158136 A1* | 8/2004 | Gough ............... | A61B 5/14546 604/82 |
| 2006/0039833 A1 | 2/2006 | Yong | |

(Continued)

OTHER PUBLICATIONS

ISR; European Patent Office; NL Nov. 15, 2019.

*Primary Examiner* — Etsub D Berhanu
*Assistant Examiner* — Destiny J Cruickshank
(74) *Attorney, Agent, or Firm* — Patshegen IP; Moshe Pinchas

(57) ABSTRACT

A fluid collection device having a specimen collection tube assembly. The specimen collection tube assembly includes a barrel defining a first chamber and an inner tube or plunger defining a second chamber. The barrel includes a luer tip at one end, and another end is in slidable sealing engagement with the inner tube (220) defining a closed system thereof. The inner tube includes a luer tip at one end, and the opposite end is equipped with a seal separating the first and second chambers in the closed system. A conduit is selectively provided either at the luer tip of the inner tube extended towards the second chamber or from the luer tip of the barrel extended towards the first chamber. The luer tip (214) of the barrel and the luer tip of the inner tube are releasably provided with at least one luer knob.

28 Claims, 14 Drawing Sheets

(56) References Cited

U.S. PATENT DOCUMENTS

2011/0097250 A1    4/2011  Yong
2017/0153165 A1*  6/2017  Nwadigo .............. B01L 3/0231

* cited by examiner

FLUID COLLECTION DEVICE

FIELD OF INVENTION

The present invention relates to a specimen collection device, and more particularly to a fluid collection device for laboratory analysis purposes.

BACKGROUND OF INVENTION

Urine or fluid samples collection for testing is usually performed by giving a person who receives medical treatment a container to urinate to provide a sample. However, the person who receives medical treatment often inadvertently soil their hands when attempting to urinate or to provide a sample into the container. This is particularly challenging for a female to manoeuvre the container into position and to keep it in place in a dignified fashion to provide the urine sample without soiling their hands. A portion of the sample will subsequently be transferred into other receptacles such as a test tube for laboratory test and analysis. This can be a very tedious process as a potential spill or splash of the sample may be involved, or otherwise, create exposure to a possibly hazardous sample.

The transfer of the sample from the container to other receptacles under uncontaminated conditions is challenging. Such methods including pouring, pipetting and funneling the sample from the container to a test tube or other receptacles are often disadvantageous because the microbiological and chemical integrity of the original sample may be sacrificed if aseptic techniques are not conformed. Additionally, the increased possibility of mislabeling of the container and/or test tube or receptacles may occur with each transfer leading to erroneous results for a particular patient.

Various attempts have been made to improve the urine or fluid samples specifically biological fluid collection devices. However, most attempts have not been completely satisfactory for one or more reasons. For example, some of the urine or fluid samples collection devices are unsatisfactory because of their designs, configurations, materials or parts appear to have certain drawbacks, such that they have not become widely used. Some attempts include devices providing a cannula attached to a collection container and to the lid through which fluid can be transferred from the container to a separate test tube. This may reduce the possibility of spillage or contamination of the sample during the transfer. However, transfer of an aliquot from the collection vessel requires an additional device and step with skilled technical assistance. Moreover, the specimen may remain suspect after the transfer is accomplished as the time interval between collection and specimen transfer can be variable and dependent on human efficiency.

The following show major disadvantages of existing conventional specimen collection devices such as, for example:

a) Difficulty of implementation by person who receives medical treatment, especially by a female who is obese or pregnant, to urinate into such a specimen collection cup without spillage or hand contamination due to the nature of female anatomy.

b) Potential spillage of the collected urine-sample especially for many elderly or infirm patients significantly increases the possibility of contamination, potentially rendering the urine-specimen useless through giving a false-analysis or a false diagnosis. Such a false-analysis requires a subsequent urine sample being taken thereby significantly increasing the total cost of the whole procedure.

c) Specimen contamination or spillage of the urine-specimen by the medical staff. Lab assistants may be exposed to urine samples and are prone to the risk of nosocomial diseases during the transfer of samples from the container to a separate test tube.

d) Inaccurate and low efficiency due to manual handling of transfer process. The transfer of an aliquot from the collection vessel requires an additional device, step and time with skilled technical assistance.

Some prior art provide a body fluid collecting receptacle and a handle for supporting the receptacle in a fluid collection position, wherein the handle includes a fluid sample chamber in fluid communication with the receptacle to receive a sample of the body fluid. Accordingly, the handle is removable from the receptacle for transport and for dispensing the body fluid sample through a tip. The handle is further provided with a flexible hollow streaker at the tip to enable the fluid sample to streak from the chamber onto an agar plate or the like.

U.S. Pat. No. 3,706,305 A discloses an elongated, unitary, blood sampling vacuum syringe, centrifuge container and specimen cup combination for use with an ordinary tubular needle holder for vacuum drawing a blood sample into the centrifuge container. This includes means for automatically withdrawing a predetermined quantity of subsequently centrifuged blood serum in the container into the specimen cup for analysis upon the manual manipulation of the device.

United States Patent Publication No.: US 2003/0105414 A1 discloses a needle assembly for multiple sample blood collection that allows a phlebotomist to determine whether vein entry has occurred when collecting a blood sample from a patient into an evacuated blood collection tube.

United States Patent Publication No.: US 2006/0039833 A1 discloses a body fluid collecting, transporting, and dispensing system including a body fluid collecting receptacle and a syringe that can serve as a handle when connected to a stout of the receptacle. A plunger of the syringe includes a head that provides a slidable sealed engagement with an inner surface of an outer barrel of the syringe for aspirating a fluid into the barrel when the plunger is pulled outwardly. The plunger is detachable from the head, such that when the fluid is transferred to the barrel, the plunger can be detached and the head remains as a sealant cover to the barrel.

United States Patent Publication No.: US 2011/0097250 A1 discloses a safety, biodegradable biological sample collection system comprising a collection container including a detachable hollow handle. The handle includes a flexible top portion which when compressed creates a vacuum within a hollow body portion of the handle and draws the sample into the handle from the container. The handle can be detached and then the sample contained in the handle can be transferred to another device for analysis.

However, none of conventional body fluid collection receptacle has considered the separation of residual specimen and sediment of urine sample within a dual-chamber vessel to eliminate the manual transfer of sedimented aliquot from the container to a separate test tube for further testing and analysis.

In view of the foregoing and other disadvantages, it is desirous to provide an improved fluid collection device for laboratory analysis purposes. Accordingly, the aspects of preferred embodiment of the present invention are designed to address one or more of the foregoing drawbacks and issues relative to prior art in an efficient and cost-effective manner. The present invention and its combination of features thereof will be described and exemplified in the detailed description.

SUMMARY OF THE INVENTION

This invention relates primarily to a fluid collection device for laboratory analysis. Accordingly, the fluid collection device includes a specimen collection tube assembly; characterised in that the specimen collection tube assembly comprises: a) a barrel defining a first chamber; b) an inner tube or plunger defining a second chamber. It should be noted that the barrel is provided with a luer tip at one end, and another end is in slidable sealing engagement with the inner tube defining a closed system thereof. The inner tube is provided with a luer tip at one end, and the opposite end is equipped with a seal separating the first and second chambers in said closed system. It should be noted that a conduit is selectively provided either at the luer tip of the inner tube extended towards the second chamber or from the luer tip of the barrel extended towards the first chamber.

The luer tip of the barrel and the luer tip of the inner tube are releasably provided with at least one luer knob, such that the luer knob can be selectively loosened or tightened for negative pressure release in the closed system to allow fluid drop under the gravity.

In the preferred exemplary of the present invention, the specimen collection tube assembly is adapted to collaboratively connect with a specimen collection cup for a specimen or fluid collection. Under such circumstance, the specimen or fluid collection may include urine or the like.

Optionally but not limiting to the invention, the specimen collection tube assembly is adapted to independently aspirate a fluid through a hypodermic needle attached to the luer tip of the barrel. Under such circumstance, the specimen or fluid collection may include biological fluid such as serum, plasma, blood, saliva, interstitial fluid or cytosol, and the like but not limited to others.

In the preferred exemplary, the specimen collection tube assembly is adapted to be connected via the luer tip of the barrel to a spout of the specimen collection cup. By way of example, but not limitation the spout of the specimen collection cup is provided with a luer lock. It will be appreciated that the specimen collection cup is preferably equipped with a cover which comes with a pressure release mechanism to release vacuum or negative pressure within the specimen collection cup. Accordingly, the pressure release mechanism includes a luer knob for pressure release during aspiration process.

It should be noted that the specimen collection tube assembly is adapted to aspirate the fluid from the specimen collection cup to the first chamber of the barrel by a vacuum suction created through a pulling action of the inner tube with the luer knob tightened. At this point, the luer knob at the cover of the specimen collection cup is loosened to release negative pressure within the specimen collection cup. It should be noted that this aspiration process is executed only after the pressure release mechanism at the cover of the specimen collection cup is activated.

In accordance with a first preferred exemplary of the present invention, the fluid is adapted to flow from the first chamber into the second chamber by turning-over the specimen collection tube assembly, such that barrel end is facing up and inner tube end is facing down; and with the luer knob tightened at the luer tip of the inner tube whilst leaving the luer tip of the barrel open to allow pressure release from the first chamber of the specimen collection tube assembly.

Accordingly, the barrel is fully pushed towards the inner tube of the specimen collection tube assembly and the luer tip of the barrel is being tightened with the luer knob that is detached from the cover before entering into a centrifuge for fluid separation process. It should be noted that the specimen collection tube assembly is adapted to be inserted into a centrifuge with the inner tube end facing inside a holder of the centrifuge for the fluid separation process. It will be appreciated that a layer of specimen residue and a layer of specimen sediment are obtained through the centrifuge separation process.

It must be noted that the specimen residue is adapted to be discharged from the second chamber of the inner tube through the conduit to the luer tip of the inner tube, leaving specimen sediment of at least 1 cc left remaining in the second chamber around the conduit of the inner tube. It will be appreciated that the barrel is being pulled upward leaving a space of at least 2 mm in the first chamber of the specimen collection tube assembly.

Accordingly, the specimen residue is discharged by releasing the luer knob at the luer tip of the inner tube, and loosening the luer knob at the luer tip of the barrel to allow negative pressure release from the second chamber of the specimen collection tube assembly. It will be appreciated that the specimen sediment is evenly distributed by shaking the specimen collection tube assembly with luer knobs tightened at both ends of the luer tips of the barrel and the inner tube before being discharged.

It should be noted that the specimen sediment is adapted to be discharged from the specimen collection tube assembly through the luer tip of the barrel. Accordingly, the specimen sediment is discharged by turning-over the specimen collection tube assembly, such that barrel end is facing down and inner tube end is facing up; by releasing the luer knob at the luer tip of the barrel, and gently press the luer knob at the luer tip of the inner tube to allow droplets of the specimen sediment to be released from the specimen collection tube assembly.

Preferably, but not limited to, the specimen sediment is discharged by droplets from the specimen collection tube assembly onto a Petri dish for microscopic analysis.

In accordance with a second preferred exemplary of the present invention, the fluid is adapted to flow from the first chamber into the second chamber by a pushing action of the inner tube towards the first chamber with the luer knob that is detached from the cover tightened at luer tip of the barrel whilst loosening the luer knob at the luer tip of the inner tube to allow pressure release from the second chamber of the specimen collection tube assembly.

Accordingly, the luer knob at the luer tip of the inner tube is being tightened before entering into a centrifuge for fluid separation process. It should be noted that the specimen collection tube assembly is adapted to be inserted into a centrifuge with the barrel end facing inside a holder of the centrifuge for the fluid separation process. It will be appreciated that a layer of specimen residue and a layer of specimen sediment are obtained through the centrifuge separation process.

It must be noted that the specimen residue is adapted to be discharged from the second chamber of the inner tube through the conduit to the luer tip of the barrel, leaving specimen sediment of at least 1 cc left remaining between the conduit in the barrel and the first chamber of the specimen collection tube assembly. Accordingly, the specimen residue is discharged by releasing the luer knob at the luer tip of the barrel, and sparingly loosening the luer knob at the luer tip of the inner tube to allow negative pressure release from the second chamber of the specimen collection tube assembly.

It should be noted that the specimen sediment is adapted to be discharged from the second chamber of the specimen collection tube assembly through the luer tip of the inner tube. It will be appreciated that the specimen sediment is evenly distributed by shaking the specimen collection tube assembly with luer knobs tightened at both ends of the luer tips of the barrel and the inner tube before being discharged. Accordingly, the specimen sediment is discharged by turning-over the specimen collection tube assembly, such that barrel end is facing up and inner tube end is facing down; by releasing the luer knob at the luer tip of the inner tube, and sparingly loosening the luer knob at the luer tip of the barrel to allow negative pressure release from the second chamber of the specimen collection tube assembly.

Preferably, but not limited to, the specimen sediment is discharged by droplets from the specimen collection tube assembly onto a Petri dish for microscopic analysis.

The present invention also provides a fluid collection method for the fluid collection device as aforementioned with a conduit either provided at the luer tip of the inner tube extended towards the second chamber or from the luer tip of the barrel extended towards the first chamber.

The present invention consists of several novel features and a combination of parts hereinafter fully described and illustrated in the accompanying description and drawings, it being understood that various changes in the details may be made without departing from the scope of the invention or sacrificing any of the advantages of the present invention.

BRIEF DESCRIPTION OF THE DRAWINGS

It will be understood that several of the drawings are merely schematic representations of the present disclosure. As such, some of the components may have been distorted from their actual scale for pictorial clarity.

The present invention will be fully understood from the detailed description given hereinbelow and the accompanying drawings which are given by way of illustration only, and thus are not limitative of the present invention, wherein.

DETAILED DESCRIPTION OF THE PREFERRED EMBODIMENTS

The present invention relates to a fluid collection device for laboratory analysis purposes. Hereinafter, this specification will describe the present invention according to the preferred exemplary of the present invention. However, it is to be understood that limiting the description to the preferred exemplary of the invention is merely to facilitate discussion of the present invention and it is envisioned that those skilled in the art may devise various modifications and equivalents without departing from the scope of the appended claims.

The word "exemplary" is used herein to mean serving as an example, instance, or illustration. Any embodiment described herein as "exemplary" is not necessarily to be construed as preferred or advantageous over other embodiments. Likewise, the term "embodiment" of a system, apparatus, device or article of manufacture does not require that all embodiments of the invention include the described components, structure, features, functionality, processes, advantages, benefits, or modes of operation.

The detailed description set forth below in connection with the appended drawings is intended as a description of various exemplary embodiments of the present invention and is not intended to represent the only embodiments in which the present invention may be practised. The detailed description includes specific details for the purpose of providing a methodical understanding of the present invention. However, it will be apparent to those skilled in the art that the present invention may be practised without these specific details. Acronyms and other descriptive terminology are used merely for convenience and clarity and are not intended to limit the scope of the invention.

For the purpose of present invention, the expressions, "specimen", "urine specimen" or "fluid"-collection device may refer to the same interpretation and may be used interchangeably. Besides, the term, "inner tube" and "plunger" may also be used interchangeably.

The present invention aims to provide an improved fluid collection device for laboratory analysis purposes, which is designed to address one or more of major limitations relative to the existing conventional specimen collection devices. Accordingly, the fluid collection device is adapted to operate with a high degree of operating reliability in a simple and cost-effective manner, which device includes: i) handle to simultaneously work as specimen tube for easy handling and collection; ii) elimination of spillage or hand contamination; iii) providing a closed system device with accurate specimen transfer method; iv) providing higher efficiency, safety and hygiene laboratory, and lending in both to economy and simplicity of manufacture, and yet higher convenience of use.

The improved fluid collection device for laboratory analysis purposes will now be described in accordance to the accompanying drawings FIGS. 1a to 26, either individually or in any combination thereof.

Figure 1A:
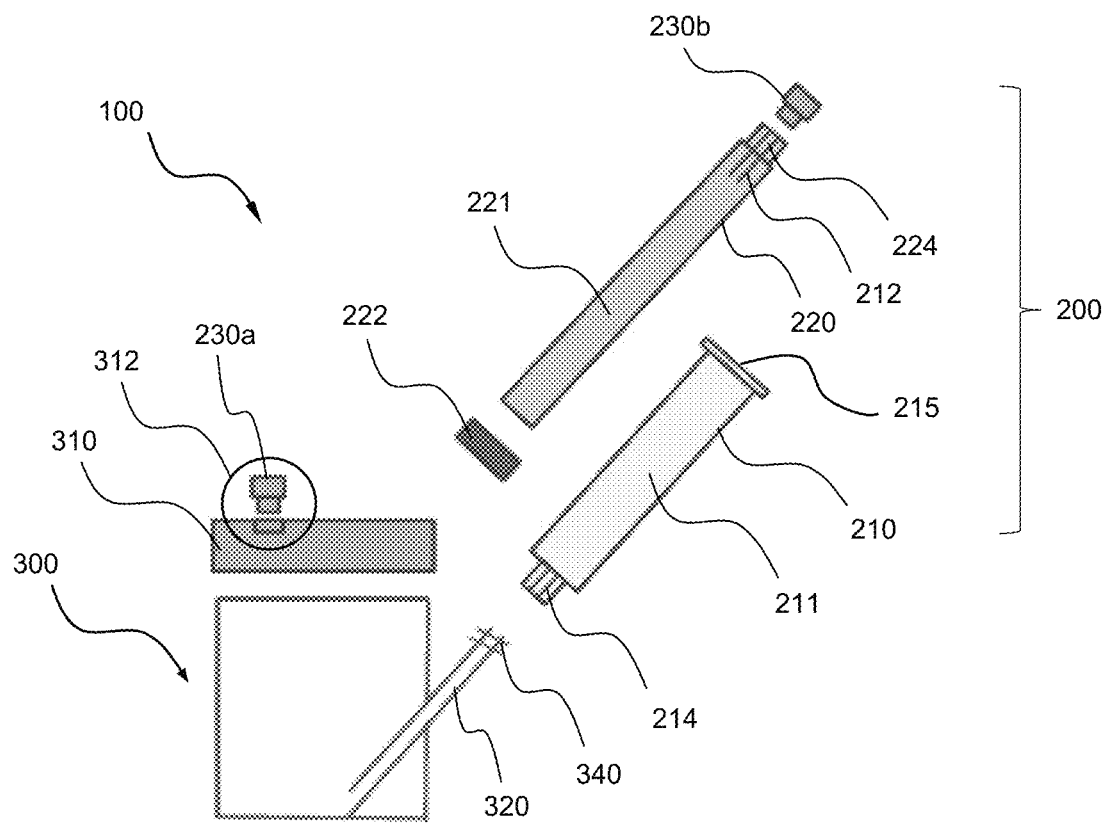
FIG. 1a is a transparent exploded view of a fluid collection device for laboratory analysis in accordance with a first preferred exemplary of the present invention.
Figure 1B:
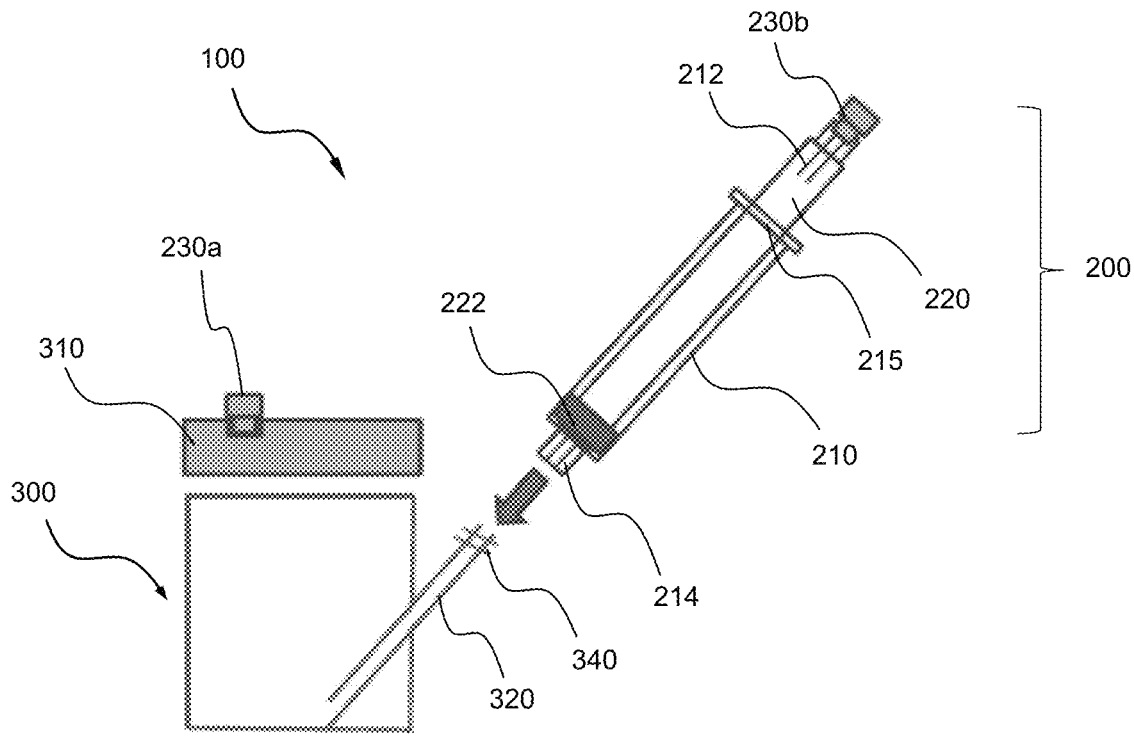
FIG. 1b shows an assembly view of a fluid collection device of FIG. 1a according to the first preferred exemplary of the present invention.

In accordance with a first preferred exemplary of the present invention, the fluid collection device (100) generally includes a specimen collection tube assembly (200) and a specimen collection cup (300) (see FIGS. 1a and 1b). Accordingly, the specimen collection tube assembly (200) comprises: a) a barrel (210) having a first chamber (211); and b) an inner tube or plunger (220) having a second chamber (221). In the preferred exemplary, the barrel (210) is provided with a luer tip (214) at one end, and another end (215) is in slidable sealing engagement with the inner tube (220) defining a closed system thereof. By way of example but not limitation, the inner tube (220) is provided with a luer tip (224) at one end, and the opposite end is equipped with a seal (222) separating the first and second chambers (211 and 221) in said closed system. It should be noted that a conduit (212) is preferably provided at the luer tip (224) of the inner tube (220) extended towards the second chamber (221) in accordance with the first preferred exemplary of the present invention.

By way of example but not limitation, the luer tip (214) of the barrel (210) and the luer tip (224) of the inner tube (220) are releasably provided with at least one luer knob (230a or 230b), such that the luer knob (230a or 230b) can be selectively loosened or tightened for negative pressure release in the closed system to allow fluid drop under the gravity. It should be noted that the luer knob (230a or 230b) although an exemplary, will be used herein in describing the configurations and functions of the present invention. However other variations, approaches or configuration, such as an air-tight, tough elastic polymeric substance or materials of same group capable of providing similar mechanical and chemical properties, to obtain desired optimal operating characteristics may be contemplated. As such, the luer knob (230a or 230b) as described herein should not be construed as limiting in any way.

It will be appreciated that the specimen collection tube assembly (200) is adapted to collaboratively connect with the specimen collection cup (300) for a specimen or fluid collection via a luer lock system. Under such circumstance, the specimen or fluid collection may include urine or the like.

Optionally but not limiting to the invention, the specimen collection tube assembly (200) is adapted to independently aspirate a fluid through a hypodermic needle attached to the luer tip (214) of the barrel (210) (not shown). Under such circumstance, the specimen or fluid specifically biological fluid collection may include serum, plasma, blood, saliva, interstitial fluid or cytosol, and the like but not limited to others.

In the preferred exemplary of the present invention, the specimen collection tube assembly (200) is adapted to be connected to a spout (320) of the specimen collection cup (300) via the luer tip (214) of the barrel (210) (see FIG. 1b). By way of example but not limitation, the spout (320) of the specimen collection cup (300) is provided with a luer lock (340) for fitting engagement with the luer tip (214) of the barrel (210). The luer lock (340) may be of a screw type or any leak-free connections, such as male and female mating type of fitting with the luer tip (214) of the barrel (210), and may be altered in a manner so as to obtain desired optimal operating characteristics.

It will be appreciated that the specimen collection cup (300) is preferably equipped with a cover (310). By way of example but not limitation, the cover (310) is preferably provided with a pressure release mechanism (312) to release vacuum or negative pressure within the specimen collection cup (300). Accordingly, the pressure release mechanism (312) includes a luer knob (230a) for pressure release during aspiration process. It should be noted that the pressure release mechanism (312) is adapted to be activated for aspiration process. Accordingly, the aspiration process is executed only after the pressure release mechanism (312) at the cover (310) of the specimen collection cup (300) is activated.

Figure 2:
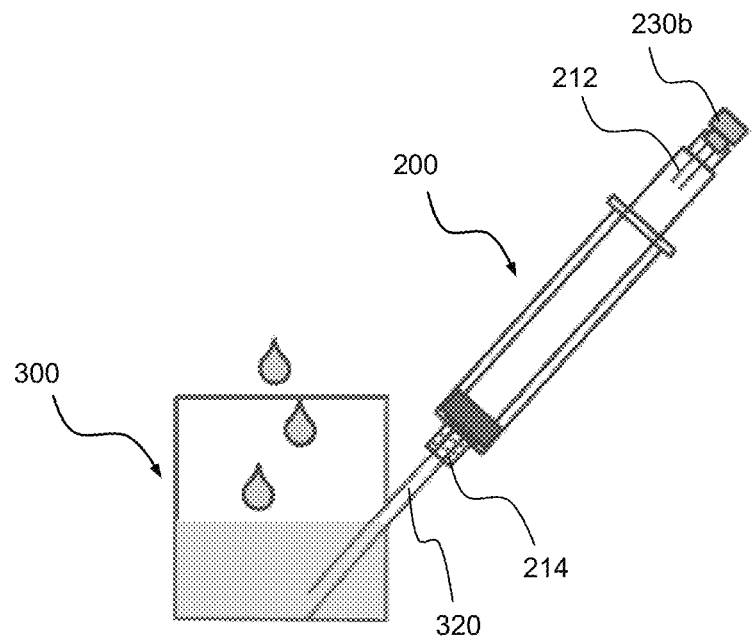
FIGS. 2 to 3 show a handling of the fluid collection device for sample collection in accordance with the first preferred exemplary of the present invention.
Figure 3:
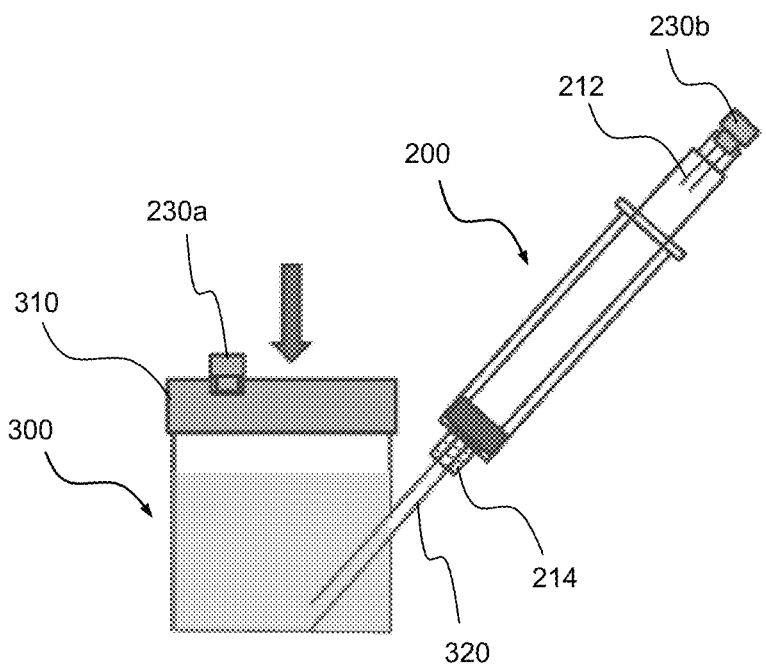
Figure 4:
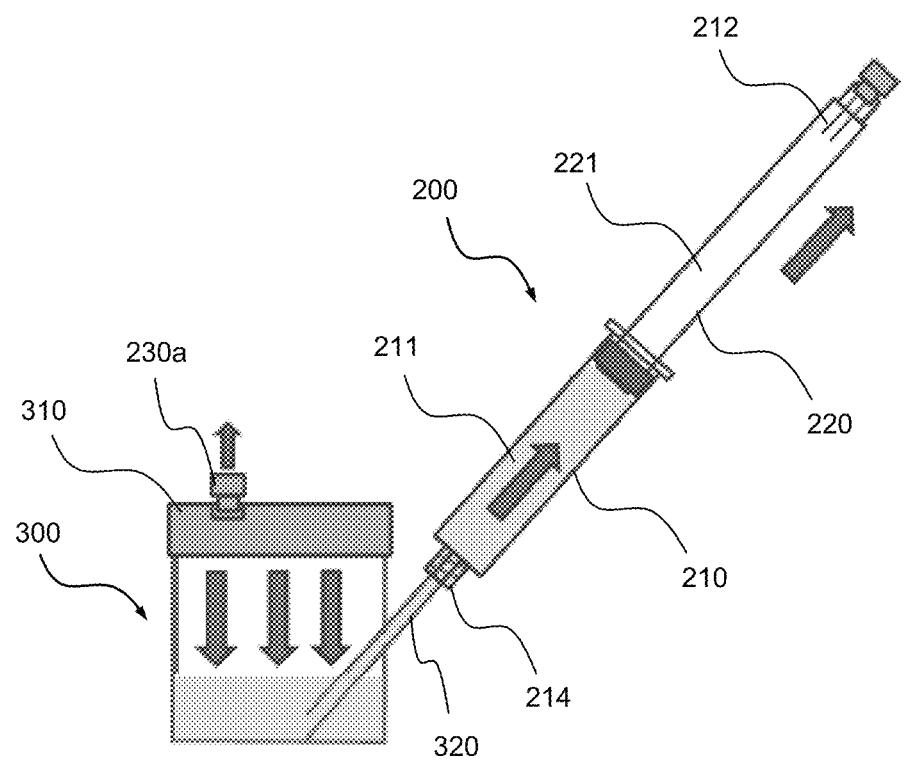
FIG. 4 shows the sample is aspirated from a specimen collection cup to a specimen collection tube assembly according to the first preferred exemplary of the present invention.
Figure 5:
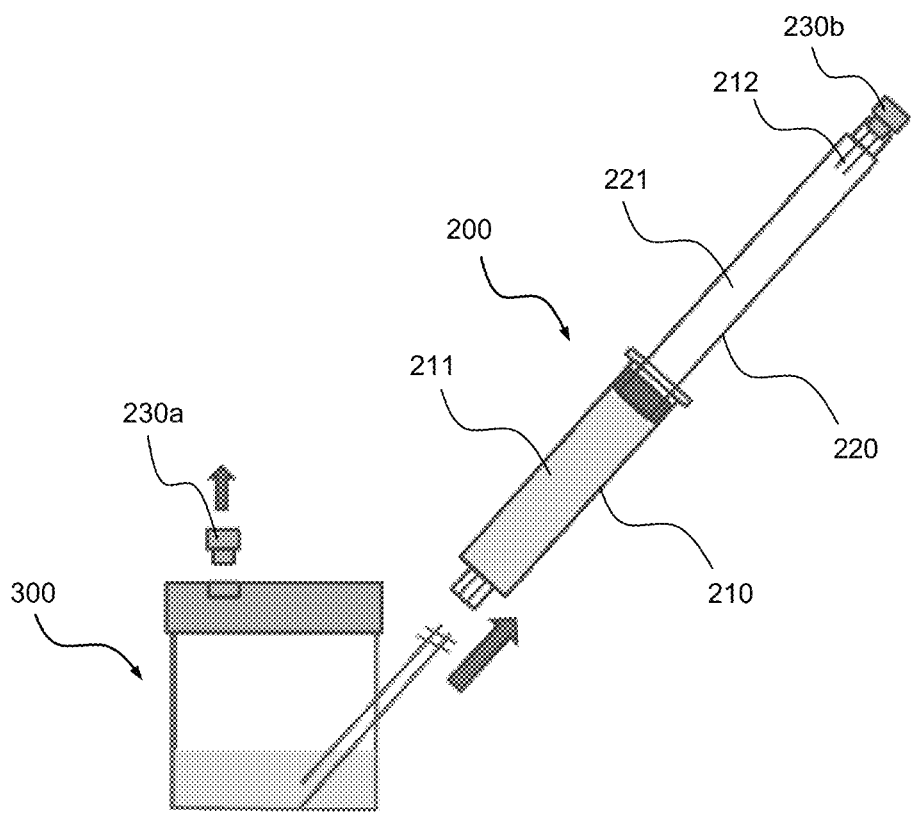
FIG. 5 shows the specimen collection tube assembly detached from the specimen collection cup in accordance with the first preferred exemplary of the present invention.
Figure 6:
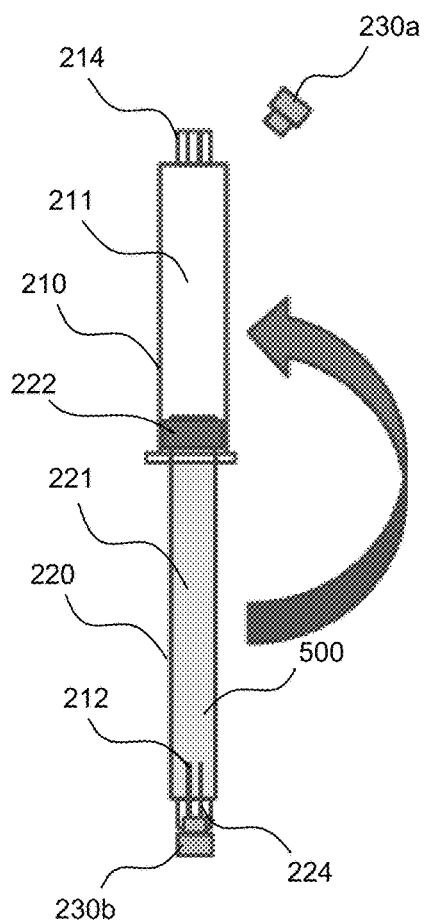
FIG. 6 shows the sample is adapted to flow from a first chamber into a second chamber by turning-over the specimen collection tube assembly according to the first preferred exemplary of the present invention.
Figure 7A:
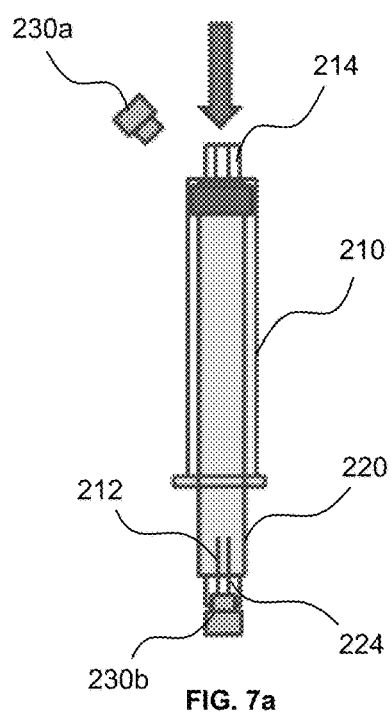
FIGS. 7a and 7b show a barrel is fully pushed towards an inner tube of the specimen collection tube assembly before entering into a centrifuge for fluid separation process in accordance to the first preferred exemplary of the present invention.
Figure 7B:
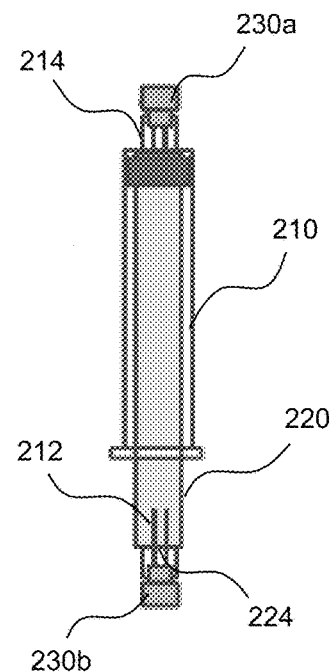

As soon as the fluid is collected into the specimen collection cup (300), the specimen collection tube assembly (200) is adapted to aspirate the fluid from the specimen collection cup (300) to the first chamber (211) of the barrel (210) by a vacuum suction created through a pulling action of the inner tube (220) with the luer knob (230b) tightened (see FIGS. 2 to 4). It will be appreciated that the aspiration process is further aided by loosening the luer knob (230a) at the cover (310) to release negative pressure in the specimen collection cup (300). At this point, the luer knob (230a) at the cover (310) of the specimen collection cup (300) is loosened to release negative pressure within the specimen collection cup (300). It will be appreciated that the specimen collection tube assembly (200) may serve as a handle for the specimen collection cup (300) for easy handling and collection of the urine specimen or fluid.

It should be noted that the fluid is adapted to flow from the first chamber (211) into the second chamber (221) by turning-over the specimen collection tube assembly (200) (see FIG. 6), such that barrel (210) end is facing up and inner tube (220) end is facing down; and with the luer knob (230b) tightened at the luer tip (224) of the inner tube (220) whilst leaving the luer tip (214) of the barrel (210) open to allow pressure release from the first chamber (211) of the specimen collection tube assembly (200). The barrel (210) will then be fully pushed towards the inner tube (220) of the specimen collection tube assembly (200) and the luer tip (214) of the barrel (210) is being tightened with the luer knob (230a) that is detached from the cover (310) before entering into a centrifuge (400) for fluid separation process (see FIGS. 7a and 7b).

Figure 8:
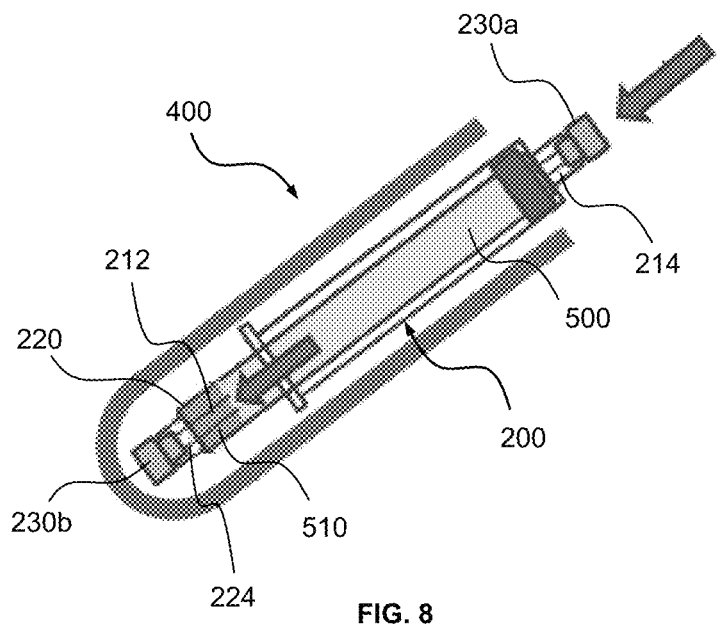
FIG. 8 shows the specimen collection tube assembly is inserted into the centrifuge the with the inner tube end facing inside a holder of the centrifuge for the fluid separation process according to the first preferred exemplary of the present invention.

By way of example but not limitation, the specimen collection tube assembly (200) is adapted to be inserted into a centrifuge with the inner tube (220) end facing inside a holder (400) of the centrifuge for the fluid separation process (see FIG. 8). It will be appreciated that a layer of specimen residue (500) and a layer of specimen sediment (510) will be obtained through the centrifuge separation process.

Figure 9A:
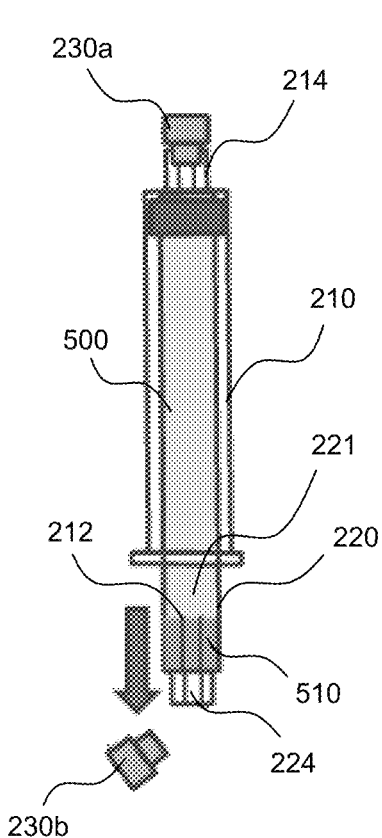
FIGS. 9a and 9b show the barrel is being pulled upward leaving a space of approximately 2 mm in the first chamber of the specimen collection tube assembly in accordance to the first preferred exemplary of the present invention.
Figure 9B:
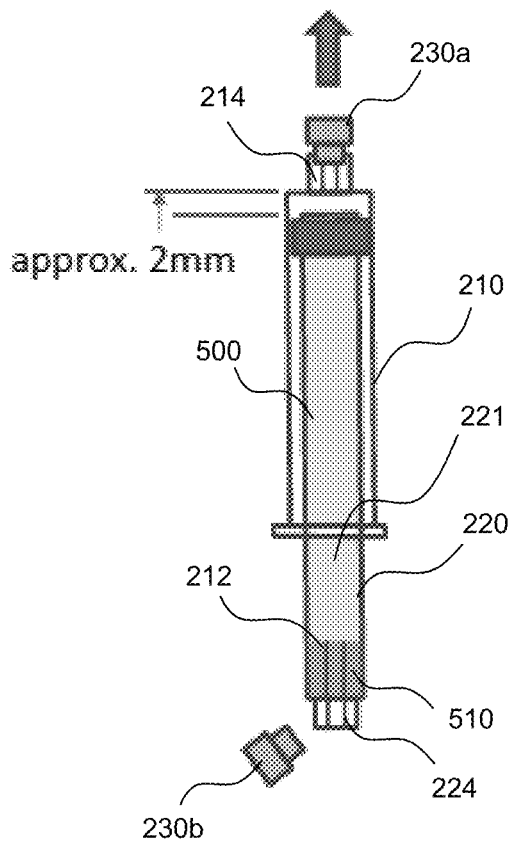
Figure 10:
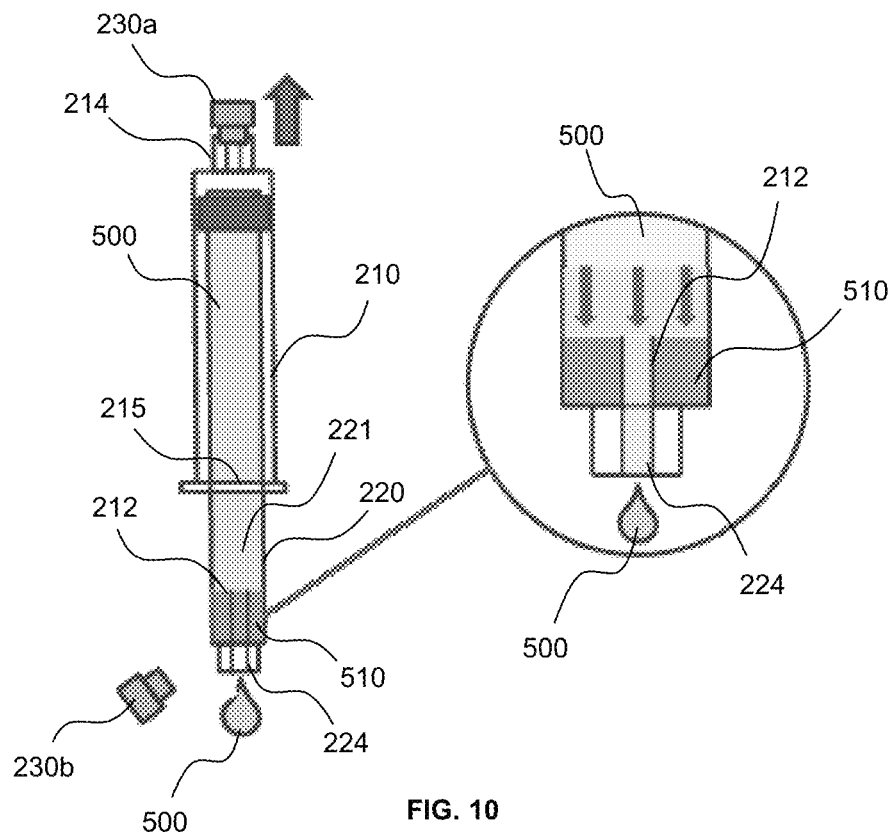
FIG. 10 shows a release of separated specimen residue from the specimen collection tube assembly in accordance with the first preferred exemplary of the present invention.
Figure 11:
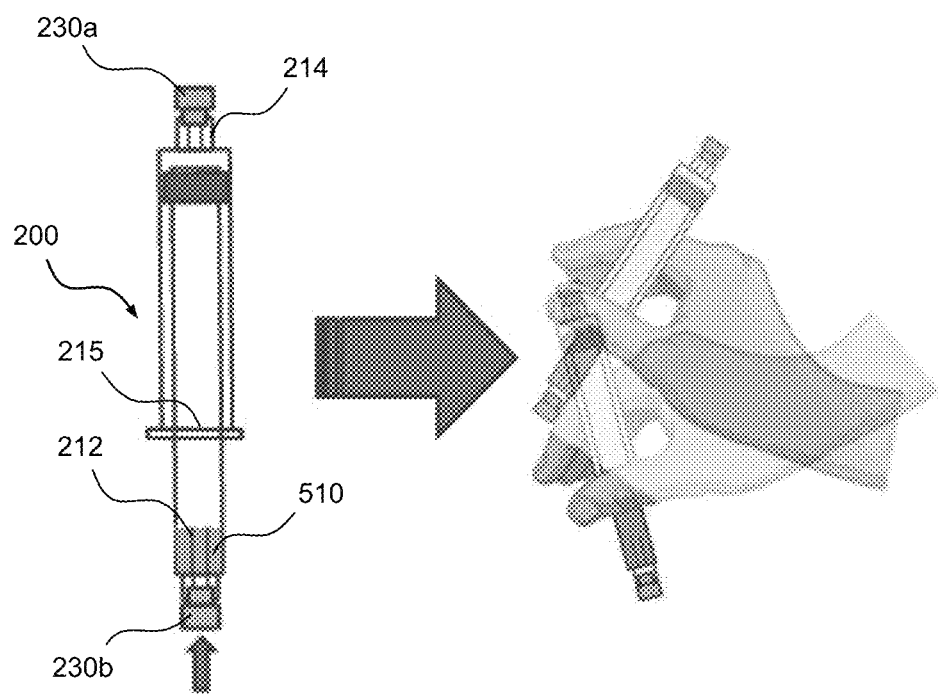
FIG. 11 shows the specimen collection tube assembly is being shaken for even distribution of specimen sediment according to the first preferred exemplary of the present invention.
Figures 12A, 12B:
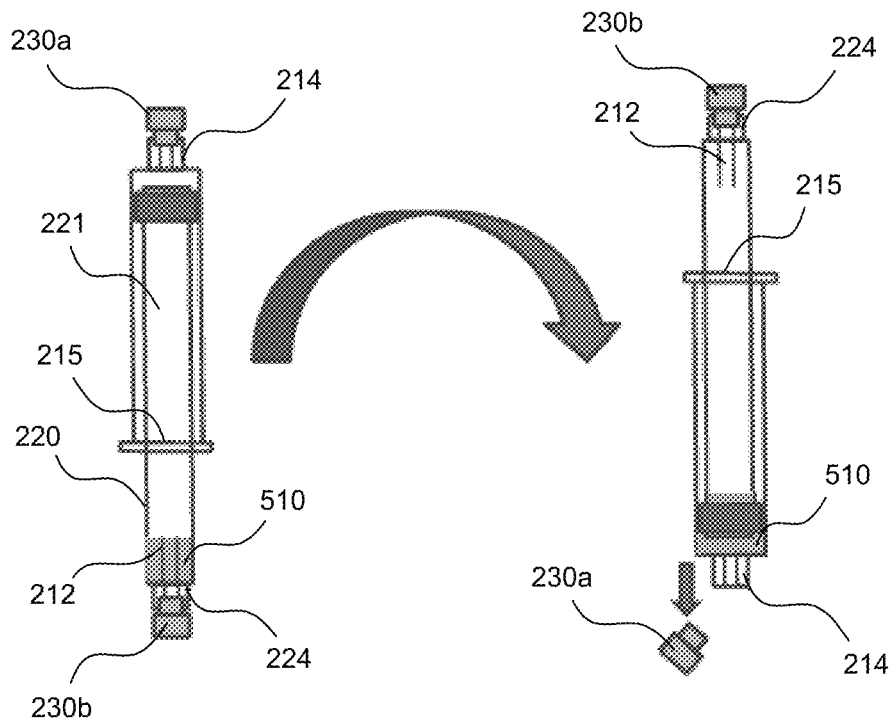
FIGS. 12a and 12b show the specimen collection tube assembly is being turned-over for the specimen sediment to be discharged in accordance with the first preferred exemplary of the present invention.
Figure 13:
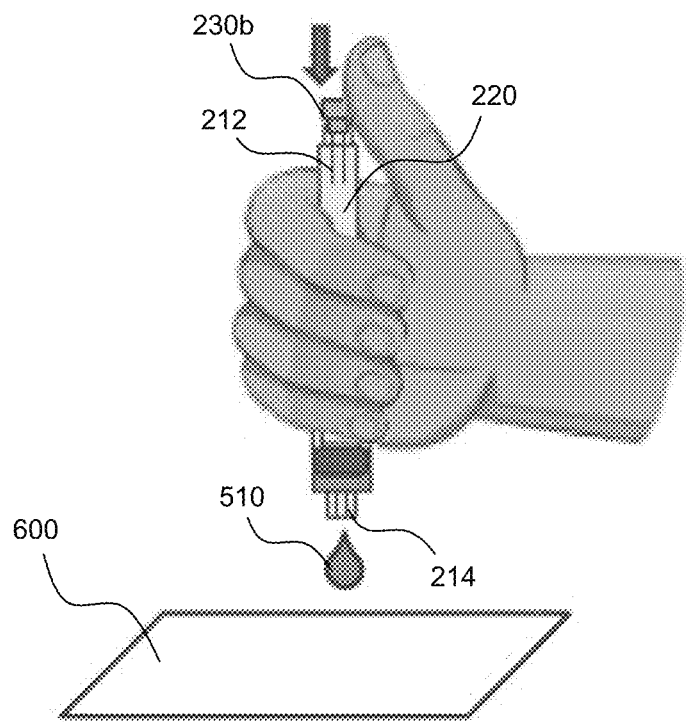
FIG. 13 shows a release of separated sediment from the specimen collection tube assembly onto Petri dish for microscopic analysis according to the first preferred exemplary of the present invention.

Referring to FIGS. 9a to 10, it should be noted that the specimen residue (500) is adapted to be discharged from the second chamber (221) of the inner tube (220) through the conduit (212) to the luer tip (224) of the inner tube (220), while enabling the specimen sediment (510) of at least 1 cc is left remaining in the second chamber (221) of the specimen collection tube assembly (200). It should also be noted that the barrel (210) is being pulled upward leaving a space of approximately or at least 2 mm in the first chamber (211) of the specimen collection tube assembly (200). The specimen residue (500) can be discharged by releasing the luer knob (230b) at the luer tip (224) of the inner tube (220), while loosening the luer knob (230a) at the luer tip (214) of the barrel (210) to allow negative pressure release from the second chamber (221) of the specimen collection tube assembly (200).

It must be noted that in the first preferred exemplary of the present invention, the specimen sediment (510) is adapted to be discharged from the second chamber (221) of the specimen collection tube assembly (200) through the luer tip (214) of the barrel (210). Accordingly, the specimen sediment (510) can be discharged by turning-over the specimen collection tube assembly (200), such that barrel (210) end is facing down and inner tube (220) end is facing up; by releasing the luer knob (230a) at the luer tip (214) of the barrel (210), and gently press the luer knob (230b) at the luer tip (224) of the inner tube (220) to allow droplets of the specimen sediment (510) to be released from the specimen collection tube assembly (200) (see FIGS. 12a to 13). Preferably, but not limited to, the specimen sediment (510) may be discharged by droplets from the specimen collection tube assembly (200) onto Petri dish (600) for microscopic analysis (see FIG. 13).

Figure 14A:
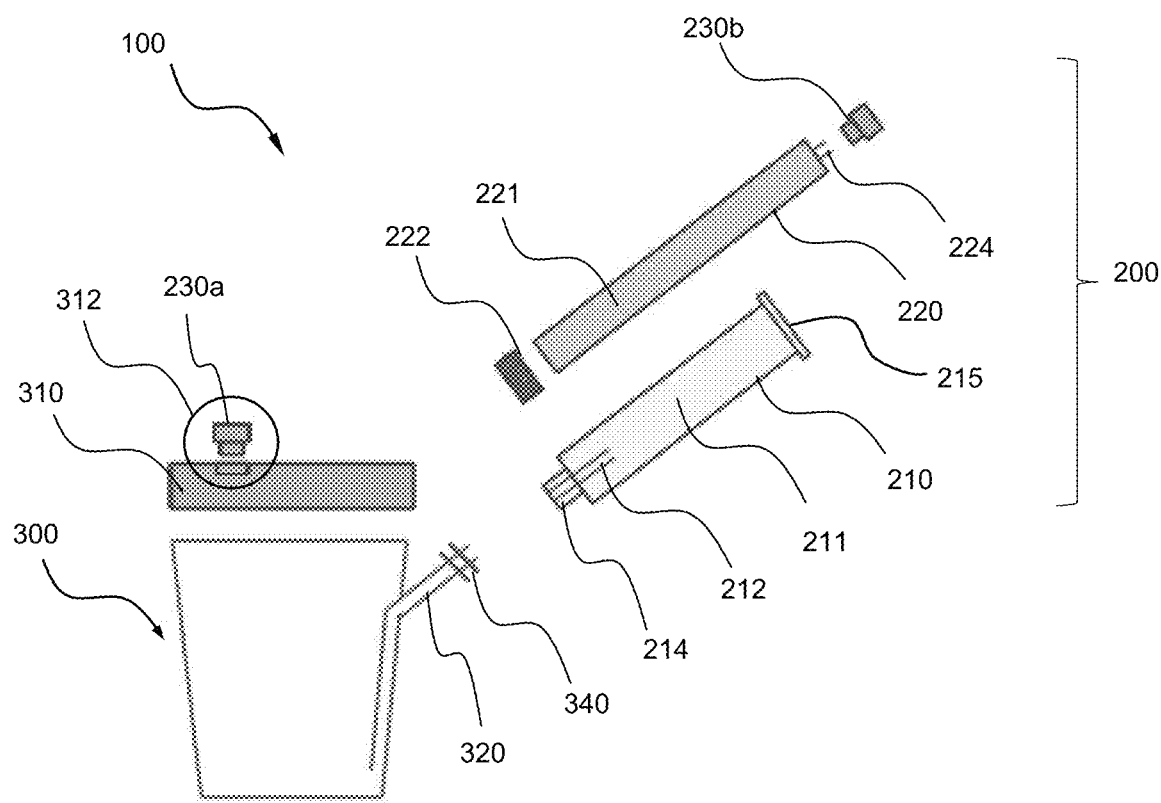
FIG. 14a is a transparent exploded view of a fluid collection device for laboratory analysis in accordance with a second preferred exemplary of the present invention.
Figure 14B:
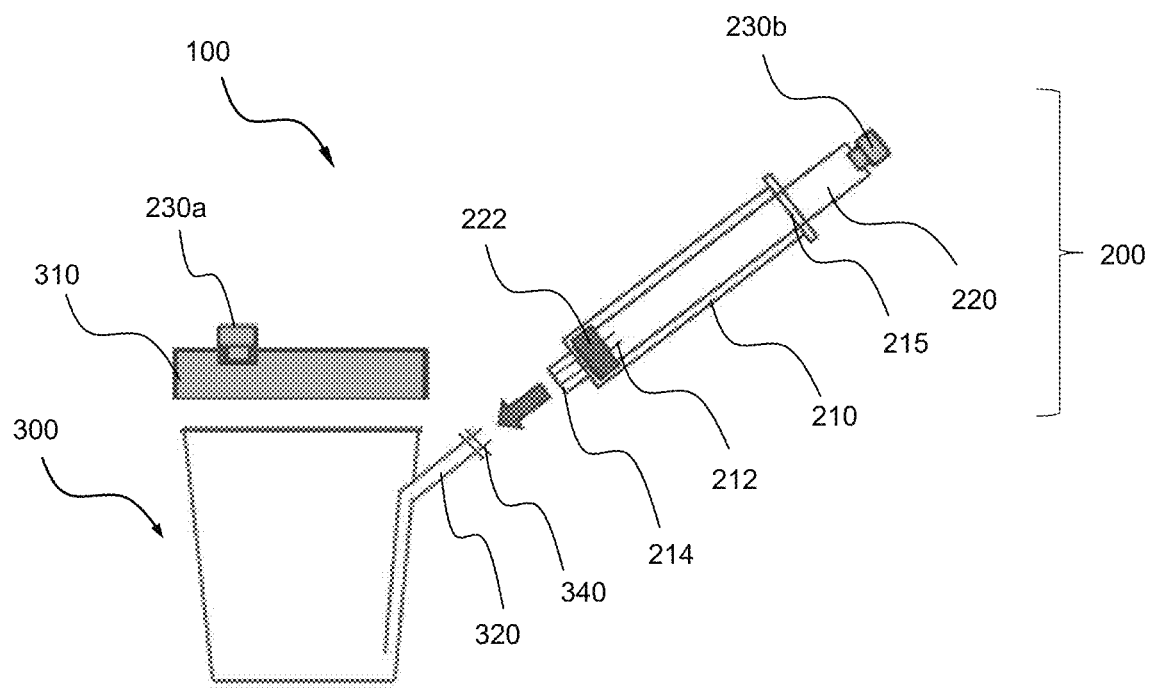
FIG. 14b shows an assembly view of a fluid collection device of FIG. 14a according to the second preferred exemplary of the present invention.

In accordance with a second preferred exemplary of the present invention, the fluid collection device (100) generally includes a specimen collection tube assembly (200) and a specimen collection cup (300) (see FIGS. 14a and 14b). Accordingly, the specimen collection tube assembly (200) comprises: a) a barrel (210) having a first chamber (211); and b) an inner tube or plunger (220) having a second chamber (221). In the preferred exemplary, the barrel (210) is provided with a luer tip (214) at one end, and another end (215) is in slidable sealing engagement with the inner tube (220) defining a closed system thereof. By way of example but not limitation, the inner tube (220) is the inner tube (220) is provided with a luer tip (224) at one end, and the opposite end is equipped with a seal (222) separating the first and second chambers (211 and 221) in said closed system. It should be noted that a conduit (212) is preferably extended from the luer tip (214) of the barrel (210) towards the first chamber (211) in accordance with the second preferred exemplary of the present invention.

By way of example but not limitation, the luer tip (214) of the barrel (210) and the luer tip (224) of the inner tube (220) are releasably provided with at least one luer knob (230a or 230b), such that the luer knob (230a or 230b) can be selectively loosened or tightened for negative pressure release in the closed system to allow fluid drop under the gravity. It should be noted that the luer knob (230a or 230b) although an exemplary, will be used herein in describing the configurations and functions of the present invention. However other variations, approaches or configuration, such as an air-tight, tough elastic polymeric substance or materials of same group capable of providing similar mechanical and chemical properties, to obtain desired optimal operating characteristics may be contemplated. As such, the luer knob (230a or 230b) as described herein should not be construed as limiting in any way.

It will be appreciated that the specimen collection tube assembly (200) is adapted to collaboratively connect with the specimen collection cup (300) for a specimen or fluid collection via a luer lock system. Under such circumstance, the specimen or fluid collection may include urine or the like.

Optionally but not limiting to the invention, the specimen collection tube assembly (200) is adapted to independently aspirate a fluid through a hypodermic needle attached to the luer tip (214) of the barrel (210) (not shown). Under such circumstance, the specimen or fluid specifically biological fluid collection may include serum, plasma, blood, saliva, interstitial fluid or cytosol, and the like but not limited to others.

In the preferred exemplary of the present invention, the specimen collection tube assembly (200) is adapted to be connected to a spout (320) of the specimen collection cup (300) via the luer tip (214) of the barrel (210) (see FIG. 14b). By way of example but not limitation, the spout (320) of the specimen collection cup (300) is provided with a luer lock (340) for fitting engagement with the luer tip (214) of the barrel (210). The luer lock (340) may be of a screw type or any leak-free connections, such as male and female mating type of fitting with the luer tip (214) of the barrel (210), and may be altered in a manner so as to obtain desired optimal operating characteristics.

It will be appreciated that the specimen collection cup (300) is preferably equipped with a cover (310). By way of example but not limitation, the cover (310) is preferably provided with a pressure release mechanism (312) to release vacuum or negative pressure within the specimen collection cup (300). Accordingly, the pressure release mechanism (312) includes a luer knob (230a) for pressure release during aspiration process. It should be noted that the pressure release mechanism (312) is adapted to be activated for aspiration process. Accordingly, the aspiration process is executed only after the pressure release mechanism (312) at the cover (310) of the specimen collection cup (300) is activated.

Figure 15:
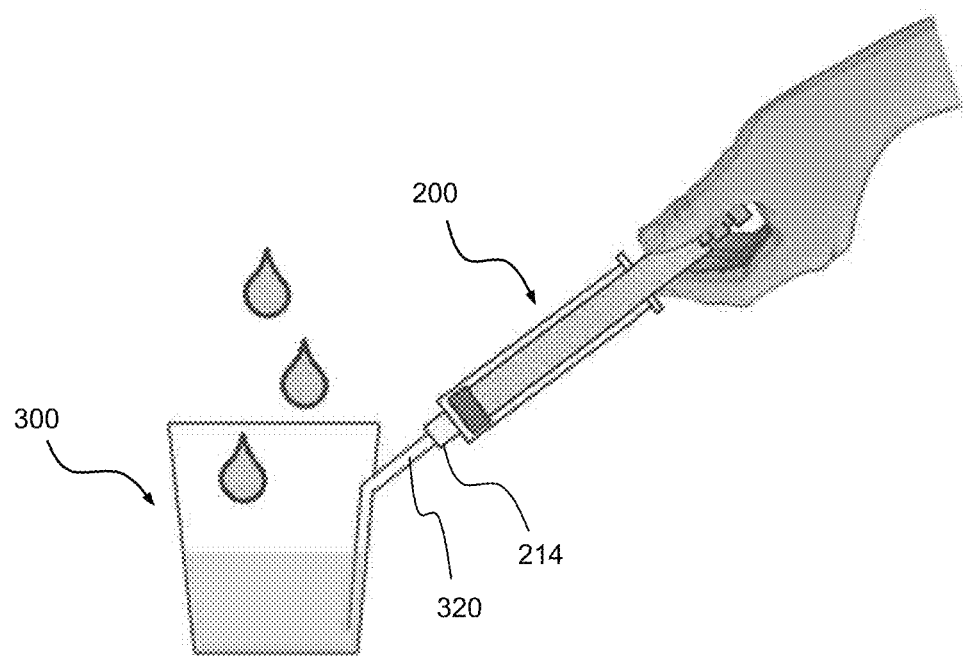
FIGS. 15 to 16 show a handling of the fluid collection device for sample collection in accordance with the second preferred exemplary of the present invention.
Figure 16:
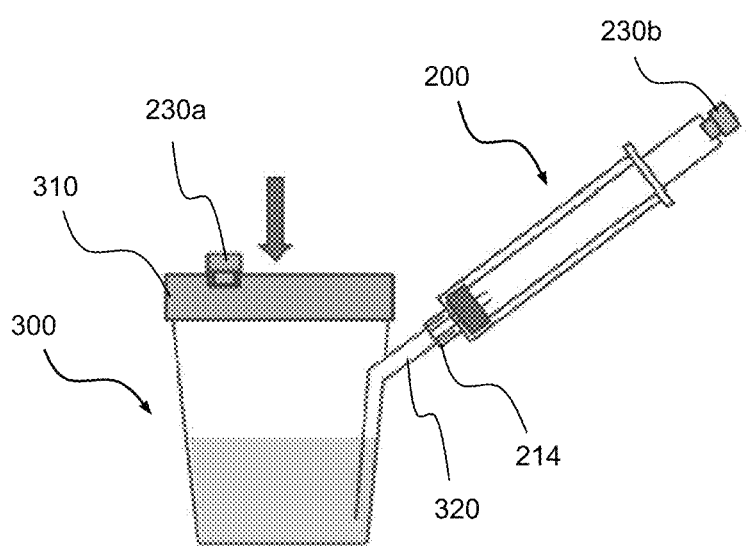
Figure 17:
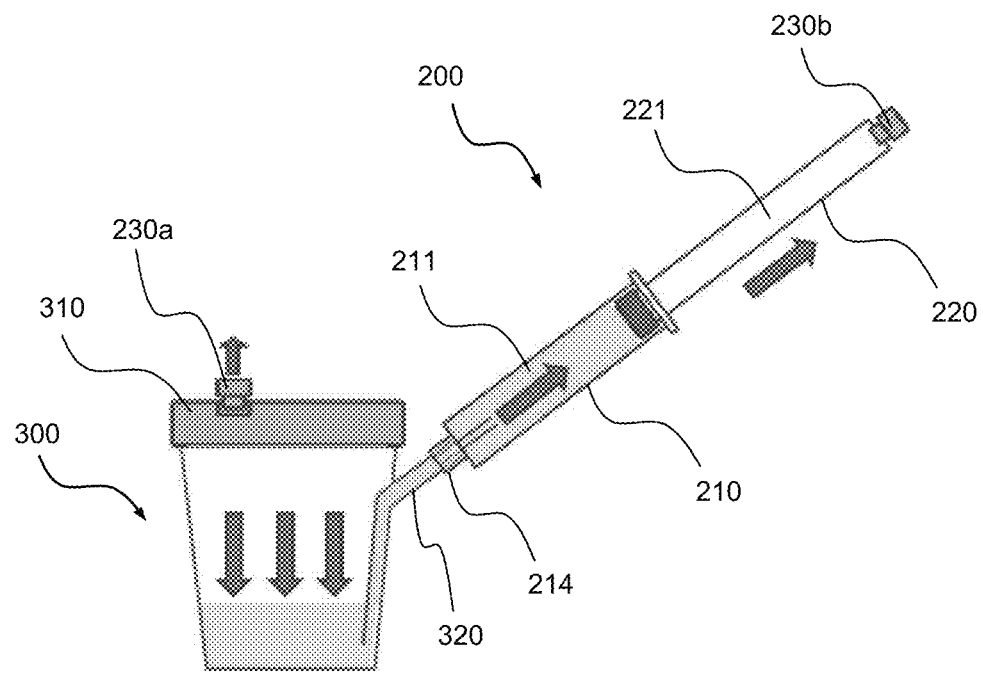
FIG. 17 shows the sample is aspirated from a specimen collection cup to a specimen collection tube assembly according to the second preferred exemplary of the present invention.

As soon as the fluid is collected into the specimen collection cup (300), the specimen collection tube assembly (200) is adapted to aspirate the fluid from the specimen collection cup (300) to the first chamber (211) of the barrel (210) by a vacuum suction created through a pulling action of the inner tube (220) with the luer knob (230b) tightened (see FIGS. 15 to 17). It will be appreciated that the aspiration process is further aided by loosening the luer knob (230a) at the cover (310) to release negative pressure in the specimen collection cup (300). At this point, the luer knob (230a) at the cover (310) of the specimen collection cup (300) is loosened to release negative pressure within the specimen collection cup (300). It will be appreciated that the specimen collection tube assembly (200) may serve as a handle for the specimen collection cup (300) for easy handling and collection of the urine specimen or fluid.

Figure 18:
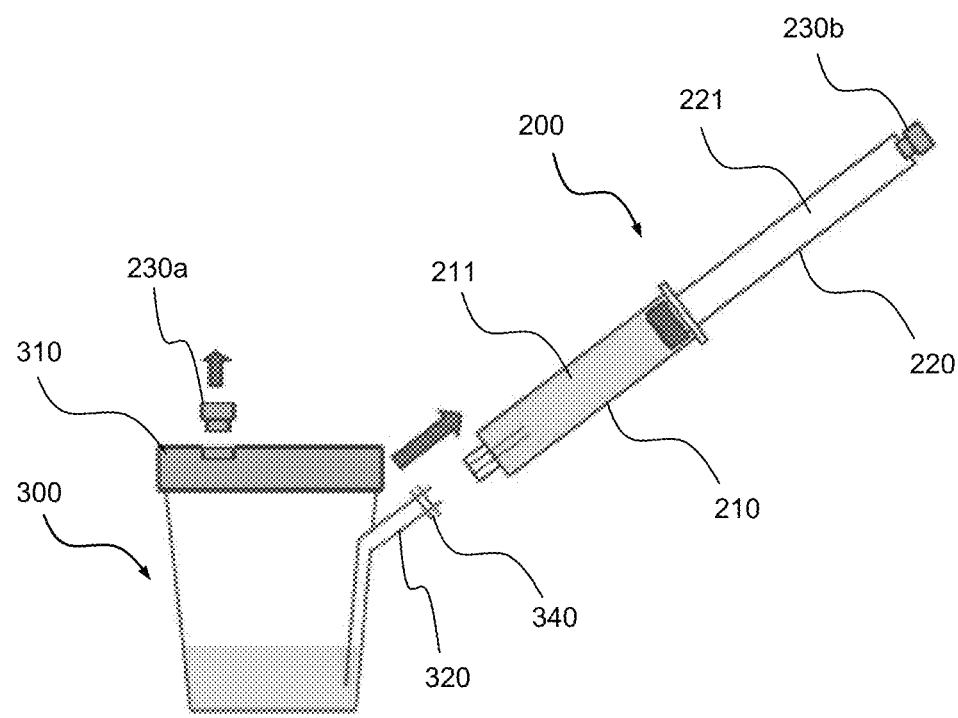
FIG. 18 shows the specimen collection tube assembly detached from the specimen collection cup in accordance with the second preferred exemplary of the present invention.
Figure 19:
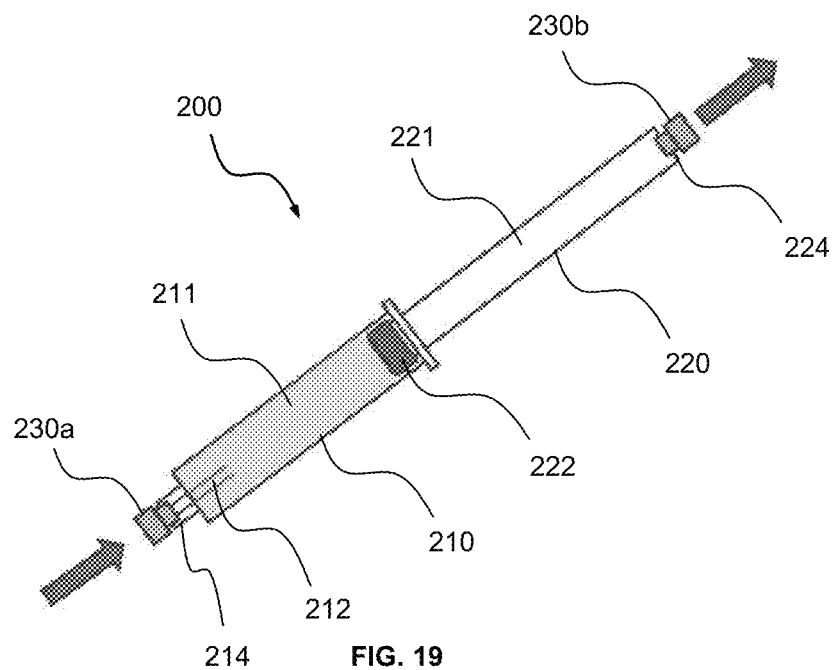
FIGS. 19 to 20 show an inner tube urged into a barrel of the specimen collection tube assembly for centrifuge or fluid separation process according to the second preferred exemplary of the present invention.
Figure 20:
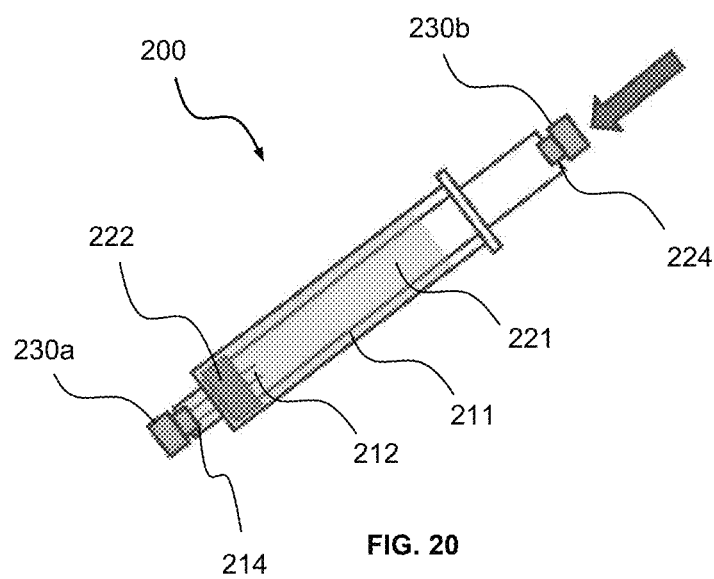

By referring to FIGS. 18 to 20, the flow of fluid from the first chamber (211) into the second chamber (221) can be attained by a pushing action of the inner tube (220) towards the first chamber (211). Accordingly, the pushing action of the inner tube (220) towards the first chamber (211) can be attained by tightening the luer knob (230a) that is detached from the cover (310) to the luer tip (214) of the barrel (210), while loosening the luer knob (230b) at the luer tip (224) of the inner tube (220) to allow pressure release from the second chamber (221) of the specimen collection tube assembly (200). It will be appreciated that the luer knob (230b) at the luer tip (224) of the inner tube (220) will then be tightened before entering into a centrifuge (400) for fluid separation process.

Figure 21:
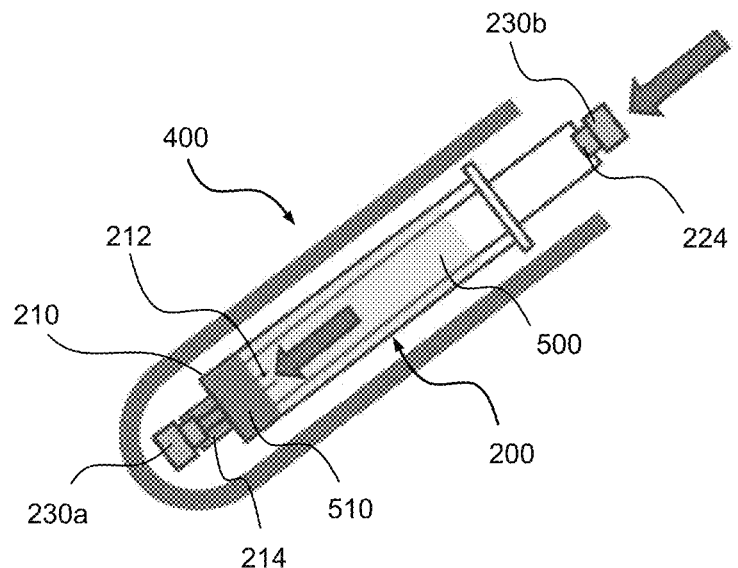
FIG. 21 shows the specimen collection tube assembly is inserted into the centrifuge with the barrel end facing inside a holder of the centrifuge for the fluid separation process in accordance with the second preferred exemplary of the present invention.

By way of example but not limitation, the specimen collection tube assembly (200) is adapted to be inserted into a centrifuge with the barrel (210) end facing inside a holder (400) of the centrifuge for the fluid separation process (see FIG. 21). It will be appreciated that a layer of specimen residue (500) and a layer of specimen sediment (510) will be obtained through the centrifuge separation process.

Figure 22:
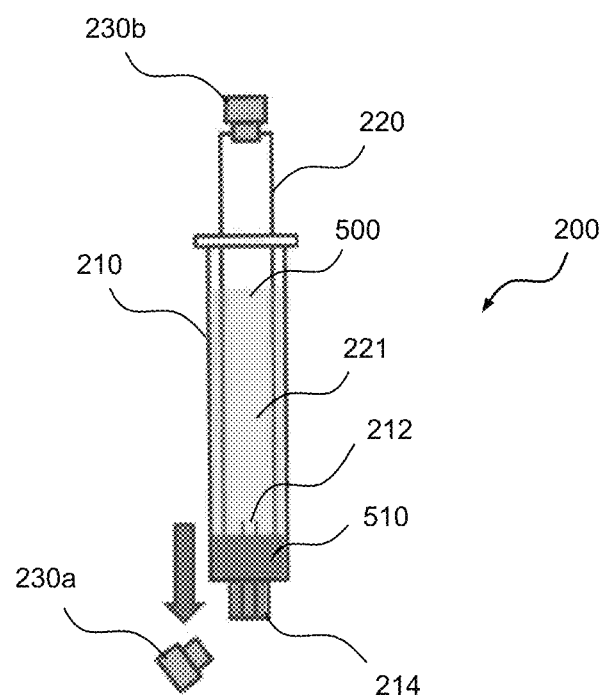
FIGS. 22 to 23 show a release of separated specimen residue from the specimen collection tube assembly in accordance with the second preferred exemplary of the present invention.
Figure 23:
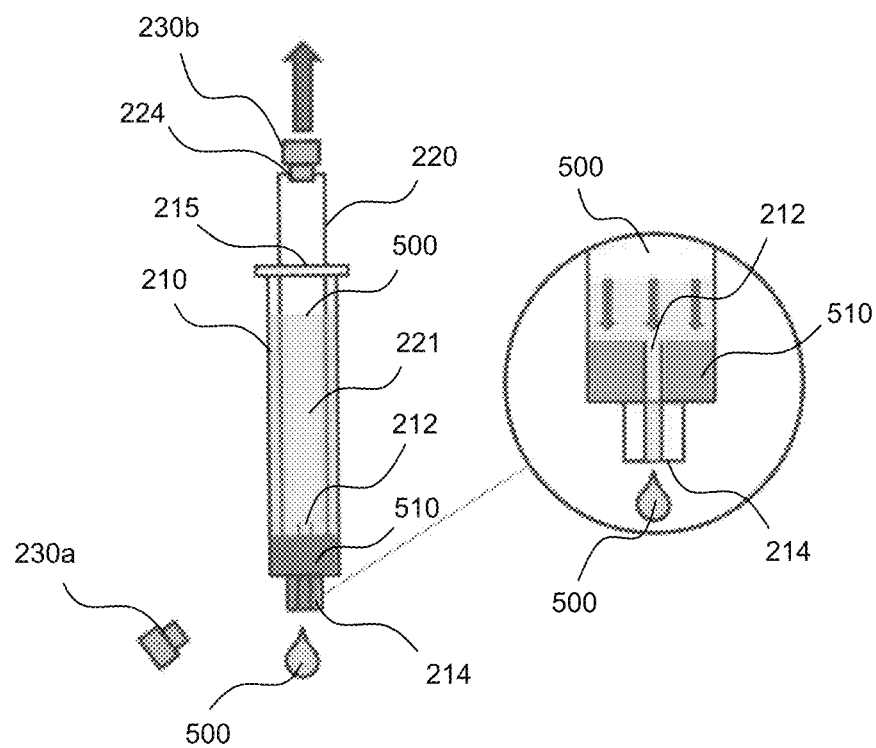
Figure 24:
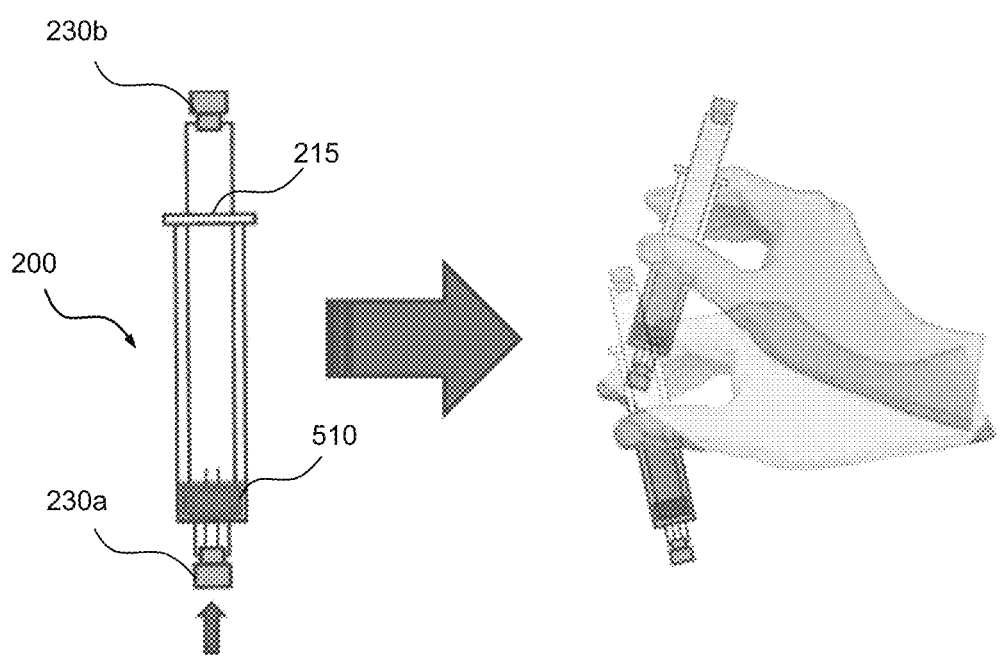
FIG. 24 shows the specimen collection tube assembly is being shaken for even distribution of specimen sediment according to the second preferred exemplary of the present invention.

Referring to FIGS. 22 and 23, it should be noted that the specimen residue (500) is adapted to be discharged from the second chamber (221) of the inner tube (220) through the conduit (212) to the luer tip (214) of the barrel (210), while enabling the specimen sediment (510) of at least 1 cc to be left remaining between the conduit (212) in the barrel (210) and the first chamber (211) of the specimen collection tube assembly (200). Accordingly, the specimen residue (500) can be discharged by releasing the luer knob (230a) at the luer tip (214) of the barrel (210), while loosening the luer knob (230b) at the luer tip (224) of the inner tube (220) to allow negative pressure release from the second chamber (221) of the specimen collection tube assembly (200).

Figures 25A, 25B:
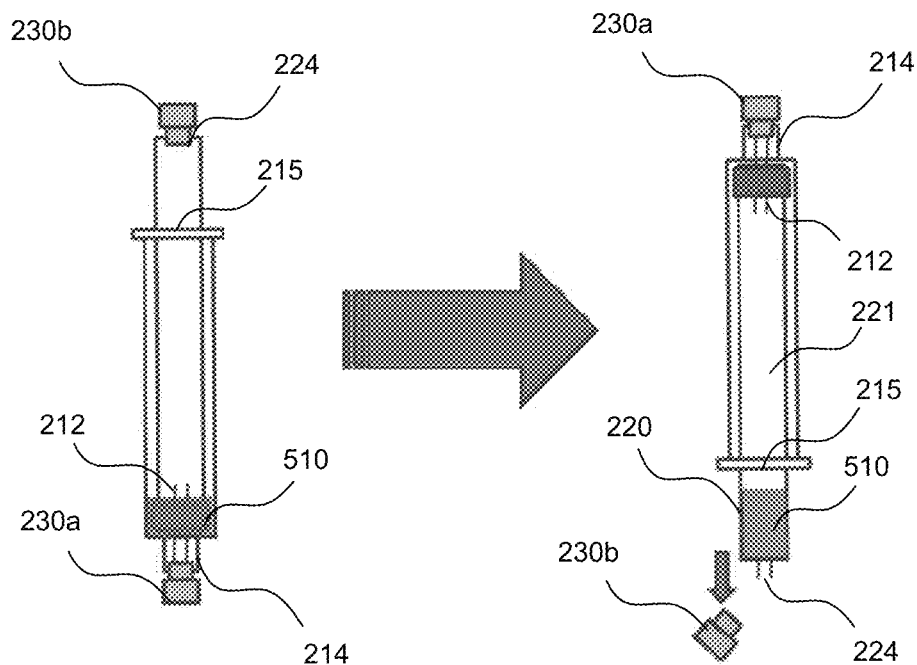
FIGS. 25a and 25b show the specimen collection tube assembly is being turned-over for the specimen sediment to be discharged in accordance with the second preferred exemplary of the present invention.
Figure 26:
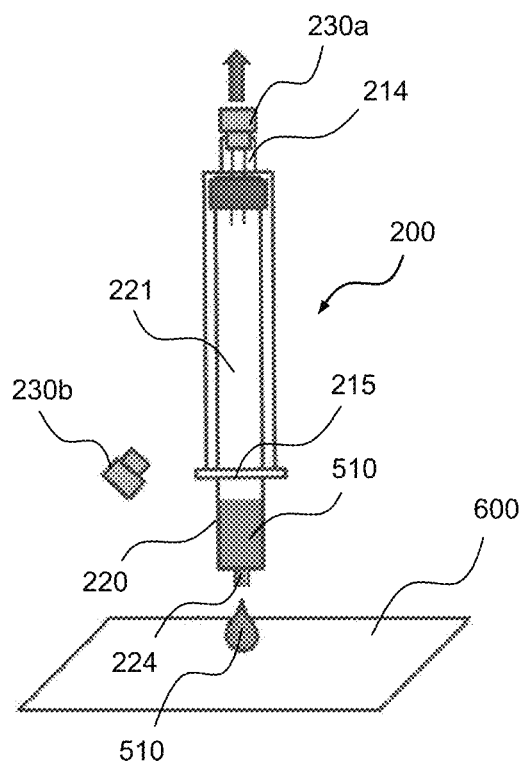
FIG. 26 shows a release of separated sediment from the specimen collection tube assembly onto Petri dish for microscopic analysis according to the second preferred exemplary of the present invention.

It must be noted that in the second preferred exemplary of the present invention, the specimen sediment (510) is adapted to be discharged from the second chamber (221) of the specimen collection tube assembly (200) through the luer tip (224) of the inner tube (220). It will be appreciated that the specimen sediment (510) is evenly distributed by shaking the specimen collection tube assembly (200) with luer knobs (230a and 230b) tightened at both ends of the luer tip (214) of the barrel (210) and the luer tip (224) of the inner tube (220) before being discharged (see FIG. 24). Accordingly, the specimen sediment (510) can be discharged by turning-over the specimen collection tube assembly (200), such that barrel (210) end is facing up and inner tube (220) end is facing down; by releasing the luer knob (230b) at the luer tip (224) of the inner tube (220), while sparingly loosening the luer knob (230a) at the luer tip (214) of the barrel (210) to allow negative pressure release from the second chamber (221) of the specimen collection tube assembly (200) (see FIGS. 25a and 25b). FIGS. 25b and 26 show the inverted position of the specimen collection tube assembly (200). Preferably, but not limited to, the specimen sediment (510) may be discharged by droplets from the specimen collection tube assembly (200) onto Petri dish (600) for microscopic analysis (see FIG. 26).

It should be noted that the configurations and arrangements of various elements used to carry out the above-mentioned system are illustrative and exemplary only and are not restrictive of the invention. One of ordinary skill in the art would recognize that those configurations, arrangements and variations used herein may be altered in a manner so as to obtain different optimal effects or desired operating characteristics. As such, the above-described should not be construed as limiting in any way, but as the best mode contemplated by the inventor for carrying out the invention.

It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" or "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations or two or more recitations).

The invention being thus described, it will be obvious that the same may be varied in many ways. Such variations are not to be regarded as a departure from the principle and scope of the invention, and all such modifications as would obvious to one skilled in the art intended to be included within the scope of following claims.

The invention claimed is:

1. A specimen collection tube assembly (200), comprising:
   i. a barrel (210) defining a first chamber (211) with a first luer tip (214) at one end and open at another end; and
   ii. an inner tube (220) in a slidable sealing engagement within the barrel (210),
   wherein the inner tube (220) defines a second chamber (221) with a second luer tip (224) at one end and open at another end;
   wherein the open end of the inner tube (220) is slidable within the first chamber (211) such that the chambers (211, 221) allow fluid transfer between one another;
   wherein a seal (222) encircles the open end of the inner tube (220) for the slidable sealing engagement within the barrel (210);
   wherein a closed system is defined within the inner tube (220) and the barrel (210) when each of the first and second luer tips (214, 224) is closed by a respective first and second luer knob (230a, 230b); and
   wherein a volume of the closed system is variable by sliding the inner tube (220) within the barrel (210).

2. The specimen collection tube assembly (200) according to claim 1, wherein each one of said first and second luer knobs (230a, 230b) can be selectively loosened or tightened for negative pressure release in the closed system to allow fluid discharge.

3. The specimen collection tube assembly (200) according to claim 1, wherein a conduit (212) is provided at at least one of the first and second luer tips (214, 224) to extend towards the corresponding chamber (211, 221).

4. The specimen collection tube assembly (200) according to claim 1, wherein the barrel (210) and the inner tube (220) are configured to aspirate a specimen or biological fluid into the first chamber (211) through the first luer tip (214), when the second luer tip (224) is closed using the second luer knob (230b) and the inner tube (220) is pulled away from the barrel (210).

5. The specimen collection tube assembly (200) according to claim 4, wherein the barrel (210) and the inner tube (220) are configured to aspirate the specimen or biological fluid through a hypodermic needle attached to the first luer tip (214) of the barrel (210).

6. The specimen collection tube assembly (200) according to claim 4, wherein the barrel (210) and the inner tube (220) are configured to aspirate the specimen or biological fluid by a vacuum suction created through a pulling action of the inner tube (220) with the second luer knob (230b) tightened to the second luer tip (224).

7. The specimen collection tube assembly (200) according to claim 4, wherein the specimen includes urine.

8. The specimen collection tube assembly (200) according to claim 4, wherein the biological fluid is selected from a group including serum, plasma, blood, saliva, interstitial fluid and cytosol.

9. The specimen collection tube assembly (200) according to claim 4, wherein a fluid in the first chamber (211) flows into the second chamber (221) through the open end of the inner tube (220) when the barrel (210) faces up and the inner tube (220) faces down.

10. The specimen collection tube assembly (200) according to claim 4, wherein biological fluid in the first chamber (211) flows into the second chamber (221), when the barrel (210) faces down and the inner tube (220) is pushed towards the first chamber (211) with the first luer knob (230a) tightened at the first luer tip (214) and the second luer knob (230b) loosened from the second luer tip (224).

11. The specimen collection tube assembly (200) according to claim 4, wherein, a conduit (212) at one of the first and second luer tips (214, 224) is configured to discharge from the second chamber (221) specimen residue (500) formed during a fluid separation process, wherein said conduit (212) is further configured to retain at least 1 cc of specimen sediment (510) formed during the fluid separation process.

12. The specimen collection tube assembly (200) according to claim 11, wherein—the specimen collection tube assembly (200) is configured to be rotated, such that the inner tube (220) faces downwards;
   the second luer knob (230b) at the second luer tip (224) of the inner tube (220) is configured to be released; and
   the first luer knob (230a) at the first luer tip (214) is configured to be loosened to release negative pressure from the second chamber (221).

13. The specimen collection tube assembly (200) according to claim 12, wherein the barrel (210) is adapted to be pulled upward to leave a space of at least 2 mm in the first chamber (211) after specimen residue (500) is discharged through the conduit (212).

14. The specimen collection tube assembly (200) according to claim 13, wherein the specimen sediment (510) is discharged through the first luer tip (214).

15. The specimen collection tube assembly (200) according to claim 13, wherein the barrel (210) and the inner tube (220) are configured to evenly distribute the specimen sediment (510) when the specimen collection tube assembly (200) is shaken with the first and second luer knobs (230a, 230b) tightened at the corresponding first and second luer tips (214, 224) after the specimen residue (500) is discharged through the conduit (212).

16. The specimen collection tube assembly (200) according to claim 15, wherein the specimen sediment (510) is discharged through the first luer tip (214) when:
   the specimen collection tube assembly (200) is rotated, such that the barrel (210) faces down and the inner tube (220) faces up;
   the first luer knob (230a) at the first luer tip (214) of the barrel (210) is released; and
   the second luer knob (230b) at the second luer tip (224) of the inner tube (220) is pressed to allow droplets of the specimen sediment (510) to be discharged through the conduit (212).

17. The specimen collection tube assembly (200) according to claim 15, wherein the specimen sediment (510) is discharged through the second luer tip (224) when:
   the specimen collection tube assembly (200) is rotated, such that barrel (210) faces up and the inner tube (220) faces down;
   the second luer knob (230b) at the second luer tip (224) of the inner tube (220) is released; and
   the first luer knob (230a) at the first luer tip (214) of the barrel (210) is loosened to release negative pressure from the second chamber (221).

18. The specimen collection tube assembly (200) according to claim 15, wherein the specimen collection tube assembly (200) is configured to discharge the specimen sediment (510) in the form of droplets through one of the first and second luer tips (214, 224).

19. The specimen collection tube assembly (200) according to claim 11, wherein the conduit (212) is at the first luer tip and wherein the specimen residue (500) is discharged through the conduit (212) at the first luer tip (214) when:
   the specimen collection tube assembly (200) is rotated, such that the inner tube (220) faces upwards;

the first luer knob (230a) at the first luer tip (214) of the barrel (210) is released; and the second luer knob (230b) at the second luer tip (224) is loosened to release negative pressure from the second chamber (221).

20. The specimen collection tube assembly (200) according to claim 19, wherein the specimen sediment (510) is discharged through the second luer tip (224).

21. A fluid collection method for laboratory analysis, the method includes:
a) providing a fluid collection device (100) including a specimen collection tube assembly (200) in accordance with claim 1 in collaborative connection with a specimen collection cup (300), wherein a conduit (212) is configured at the second luer tip (224) of the inner tube (220) of the specimen collection tube assembly (200) to extend towards the second chamber (221) of the specimen collection tube assembly (200);
b) collecting a specimen or fluid using the specimen collection cup (300);
c) aspirating the specimen or fluid using the specimen collection tube assembly (200) through a spout (320) of the specimen collection cup (300) by pulling action of the inner tube (220) with the first luer knob (230a) tightened;
d) releasing the specimen collection tube assembly (200) from the specimen collection cup (300);
e) turning-over the specimen collection tube assembly (200), such that the barrel (210) faces up and the inner tube (220) faces down to transfer the specimen or fluid to the second chamber (221);
f) pushing the barrel (210) fully towards the inner tube (220) and tightening the second luer knob (230b);
g) inserting the specimen collection tube assembly (200) into a centrifuge with the second luer tip (224) of the inner tube (220) facing an inner surface of a holder (400) of the centrifuge for a fluid separation process;
h) loosening and releasing the second luer knob (230b) at the second luer tip (224) of the inner tube (220) after removing the specimen collection tube assembly (200) from the holder (400);
i) discharging specimen residue (500) from the second chamber (221) through the conduit (212) to the second luer tip (224) of the inner tube (220), by loosening the first luer knob (230a) at the first luer tip (214) of the barrel (210) to allow negative pressure release from the second chamber (221);
j) leaving a specimen sediment (510) of at least 1 cc to remain in the second chamber (221);
k) distributing the specimen sediment (510) evenly by shaking the specimen collection tube assembly (200) with both the first and second luer knobs (230a and 230b) tightened at the corresponding first and second luer tips (214 and 224);
l) pulling the barrel (210) upward and leaving a space of at least 2 mm in the first chamber (211);
m) turning-over the specimen collection tube assembly (200), such that the barrel (210) faces down and the inner tube (220) faces up; and
n) discharging the specimen sediment (510) through the first luer tip (214) of the barrel (210) by releasing the first luer knob (230a) at the first luer tip (214) of the barrel (210), and pressing the second luer knob (230b) at the second luer tip (224) of the inner tube (220) to allow droplets of the specimen sediment (510) to be released from the specimen collection tube assembly (200).

22. A fluid collection method for laboratory analysis, the method includes:
a) providing a fluid collection device (100) including a specimen collection tube assembly (200) in accordance with claim 1 in collaborative connection with a specimen collection cup (300), wherein a conduit (212) extends from the first luer tip (214) of the barrel (210) of the specimen collection tube assembly (200) towards the first chamber (211);
b) collecting a specimen or fluid using the specimen collection cup (300);
c) aspirating the specimen or fluid using the specimen collection tube assembly (200) through a spout (320) of the specimen collection cup (300) by pulling action of the inner tube (220) of the specimen collection tube assembly (200) with the second luer knob (230b) tightened;
d) releasing the specimen collection tube assembly (200) from the specimen collection cup (300);
e) allowing the specimen or fluid to flow from the first chamber (211) into the second chamber (221) in the inner tube (220) by a pushing action of the inner tube (220) towards the first chamber (211) with the first luer knob (230a) tightened at the first luer tip (214) of the barrel (210) and with the second luer knob (230b) at the second luer tip (224) of the inner tube (220) loosened to allow pressure release from the second chamber (221) of the specimen collection tube assembly (200);
f) tightening the second luer knob (230b) at the second luer tip (224) of the inner tube (220);
g) inserting the specimen collection tube assembly (200) into a centrifuge such that the second luer tip (224) of the barrel (210) faces an inner surface of a holder (400) of the centrifuge for a fluid separation process;
h) loosening and releasing the first luer knob (230a) at the first luer tip (214) of the barrel (210) after removing the specimen collection tube assembly (200) from the holder (400);
i) discharging specimen residue (500) from the second chamber (221) of the inner tube (220) through the conduit (212) to the first luer tip (214) of the barrel (210), by loosening the second luer knob (230b) at the second luer tip (224) of the inner tube (220) to allow negative pressure release from the second chamber (221);
j) leaving a specimen sediment (510) of at least 1 cc to remain in the second chamber (221);
k) distributing the specimen sediment (510) evenly by shaking the specimen collection tube assembly (200) with both the first and second luer knobs (230a and 230b) tightened at the corresponding first and second luer tips (214 and 224);
l) turning-over the specimen collection tube assembly (200), such that the barrel (210) faces up and the inner tube (220) faces down;
m) releasing the second luer knob (230b) at the second luer tip (224) of the inner tube (220); and
n) discharging the specimen sediment (510) through the second luer tip (224) of the inner tube (220) by loosening the first luer knob (230a) at the first luer tip (214) of the barrel (210) to allow negative pressure release from the second chamber (221) of the specimen collection tube assembly (200).

23. A fluid collection device (100) for laboratory analysis, the device includes:
(i) a specimen collection cup (300) for a specimen or fluid collection; and (ii) a specimen collection tube assembly (200) in collaborative connection with the specimen collection cup (300), wherein the specimen collection tube assembly (200) comprises a barrel (210) and an inner tube or plunger (220) in a slidable sealing engagement within the barrel (210); and (iii) the barrel (210) defines a first chamber (211) and is provided with a first luer tip (214) at one end for the connection with the specimen collection cup (300) and open at the other end for receiving the inner tube (220), wherein a first luer knob (230*a*) selectively closes the first luer tip (214) of the barrel (210);

characterised in that the inner tube (220) defines a second chamber (221) and comprises:

a) a second luer tip (224) at one end, wherein the other end of the inner tube (220) is open to allow fluid transfer between the chambers (211, 221) and is slidable within the first chamber (211);

b) a seal (222) encircling the open end of the inner tube (220) for the slidable sealing engagement within the barrel (210); and c) a second luer knob (230b) for releasably closing the second luer tip (224) of the inner tube (220), wherein a closed system is defined within the inner tube (220) and the barrel (210) when the first and second luer tips (214, 224) are closed by the first and second luer knobs (230*a*, 230*b*), wherein a volume of the closed system is variable by sliding the inner tube (220) within the barrel (210).

24. The fluid collection device (100) according to claim 23, wherein the specimen collection tube assembly (200) is adapted to be connected via the first luer tip (214) of the barrel (210) to a spout (320) of the specimen collection cup (300).

25. The fluid collection device (100) according to claim 24, wherein the spout (320) of the specimen collection cup (300) is provided with a luer lock (340).

26. The fluid collection device (100) according to claim 23, wherein the specimen collection cup (300) is equipped with a cover (310).

27. The fluid collection device (100) according to claim 26, wherein the cover (310) is provided with a pressure release mechanism (312) to release vacuum or negative pressure within the specimen collection cup (300).

28. The fluid collection device (100) according to claim 27, wherein the pressure release mechanism (312) includes a luer knob for pressure release during an aspiration process.

* * * * *